United States Patent
Diaz et al.

(10) Patent No.: US 6,179,857 B1
(45) Date of Patent: *Jan. 30, 2001

(54) STRETCH RESISTANT EMBOLIC COIL WITH VARIABLE STIFFNESS

(75) Inventors: Roberto Diaz, Miami; Donald K. Jones, Lauderhill; Brett E. Naglreiter, Hollywood, all of FL (US)

(73) Assignee: Cordis Corporation, Miami Lakes, FL (US)

( * ) Notice: Under 35 U.S.C. 154(b), the term of this patent shall be extended for 0 days.

This patent is subject to a terminal disclaimer.

(21) Appl. No.: 09/256,162

(22) Filed: Feb. 22, 1999

(51) Int. Cl.⁷ .................................................. A61M 29/00
(52) U.S. Cl. ........................... 606/194; 606/1; 606/151; 606/213
(58) Field of Search ........................... 606/191, 194, 606/198, 200, 213, 151; 623/1, 11, 12; 604/104, 527

(56) References Cited

U.S. PATENT DOCUMENTS

| | | |
|---|---|---|
| 2,853,070 | 9/1958 | Julliard . |
| 3,334,629 | 8/1967 | Cohn . |
| 3,353,718 | 11/1967 | McLay . |
| 4,512,338 | 4/1985 | Balko et al. . |
| 4,743,230 | 5/1988 | Nordquest . |
| 4,832,692 | 5/1989 | Box et al. . |
| 4,919,121 | 4/1990 | Rydell et al. . |
| 4,994,069 | 2/1991 | Ritchart et al. . |
| 5,108,407 | 4/1992 | Geremia et al. . |
| 5,122,136 | 6/1992 | Guglielmi et al. . |
| 5,137,514 | 8/1992 | Ryan . |
| 5,168,757 | 12/1992 | Rabenau et al. . |
| 5,217,484 | 6/1993 | Marks . |
| 5,234,437 | 8/1993 | Sepetka . |
| 5,250,071 | 10/1993 | Palermo . |
| 5,261,916 | 11/1993 | Engelson . |
| 5,263,964 | 11/1993 | Purdy . |
| 5,304,195 | 4/1994 | Twyford, Jr. et al. . |
| 5,312,415 | 5/1994 | Palermo . |
| 5,334,210 | 8/1994 | Gianturco . |
| 5,336,183 | 8/1994 | Greelis et al. . |
| 5,342,304 | 8/1994 | Tacklind et al. . |
| 5,350,397 | 9/1994 | Palermo et al. . |
| 5,382,259 | 1/1995 | Phelps et al. . |
| 5,443,478 | 8/1995 | Purdy . |
| 5,470,317 | 11/1995 | Cananzey et al. . |
| 5,578,074 | 11/1996 | Mirigian . |
| 5,582,619 | 12/1996 | Ken . |
| 5,601,600 | 2/1997 | Ton . |
| 5,609,608 | 3/1997 | Benett et al. . |
| 5,647,847 | 7/1997 | Lafontaine et al. . |
| 5,718,711 | * 2/1998 | Berenstein et al. ............ 606/191 |
| 5,725,546 | * 3/1998 | Samson ............................ 606/191 |
| 5,853,418 | 12/1998 | Ken et al. . |
| 5,984,929 | * 11/1999 | Bashiri et al. .................. 606/108 |
| 6,063,100 | * 5/2000 | Diaz et al. ...................... 606/191 |

* cited by examiner

*Primary Examiner*—Glenn K. Dawson
*Assistant Examiner*—Jennifer Maynard
(74) *Attorney, Agent, or Firm*—Henry W. Collins

(57) ABSTRACT

An embolic coil which may be placed at a preselected location within a vessel comprising a helically wound coil in which various combinations of adjacent turns are spot welded together to create a stretch resistant coil of a preselected flexibility.

9 Claims, 2 Drawing Sheets

STRETCH RESISTANT EMBOLIC COIL WITH VARIABLE STIFFNESS

BACKGROUND OF THE INVENTION

1. Field of the Invention

The present invention relates to an embolic coil which may be placed at a preselected location within a vessel of the human body, and more particularly, relates to an embolic coil which is stretch resistant but which may be modified to vary the stiffness, or flexibility, of the coil.

2. Description of the Prior Art

For many years flexible catheters have been used to place various devices within the vessels of the human body. Such devices include dilatation balloons, radiopaque fluids, liquid medications and various types of occlusion devices such as balloons and embolic coils. Examples of such catheter devices are disclosed in U.S. Pat. No. 5,108,407, entitled "Method And Apparatus For Placement Of An Embolic Coil"; U.S. Pat. No. 5,122,136, entitled, "Endovascular Electrolytically Detachable Guidewire Tip For The Electroformation Of Thrombus In Arteries, Veins, Aneurysms, Vascular Malformations And Arteriovenous Fistulas." These patents disclose devices for delivering embolic coils to preselected position within vessel of the human body in order to treat aneurysms or alternatively to occlude the blood vessel at the particular location.

Coils which are placed in vessels may take the form of helically wound coils, or alternatively, may be random wound coils, coils wound within other coils or many other such coil configurations. Examples of various coil configurations are disclosed in U.S. Pat. No. 5,334,210, entitled, "Vascular Occlusion Assembly; U.S. Pat. No. 5,382,259, entitled, "Vasoocclusion Coil With Attached Tubular Woven Or Braided Fibrous Coverings." Embolic coils are generally formed of a radiopaque metallic materials, such as platinum, gold, tungsten or alloys of these metals. Often times several coils are placed at a given location in order to occlude the flow of blood through the vessel by promoting thrombus formation at the particular location.

In the past, the proximal end of embolic coils have been placed within the distal end of the catheter and when the distal end of the catheter is properly positioned the coil may then be pushed out of the end of the catheter with, for example a guidewire, to release the coil at the desired location. This procedure of placement of the embolic coil is conducted under fluoroscopic visualization such that the movement of the coil through the vasculature of the body may be monitored and the coil may be placed in the desired location. With these placements systems there is very little control over the exact placement of the coil since the coil may be ejected to a position some distance beyond the end of the catheter. As is apparent, with these latter systems, when the coil has been released from the catheter it is difficult, if not impossible, to retrieve the coil or to reposition the coil.

Numerous procedures have been developed to enable more accurate positioning of coils within a vessel. Still another such procedure involves the use of a glue or solder for attaching the embolic coil to a guidewire which, is in turn, placed within a flexible catheter for positioning the coil within the vessel at a preselected position. Once the coil is at the desired position, the coil is restrained by the catheter and the guidewire is pulled from the proximal end of the catheter to thereby cause the coil to be detached from the guidewire and released from the catheter system. Such a coil positioning system is disclosed in U.S. Pat. No. 5,263,964, entitled, "Coaxial Traction Detachment Apparatus And Method."

Another coil positioning system utilizes a catheter having a socket at the distal end of the catheter for retaining a ball which is bonded to the proximal end of the coil. The ball, which is larger in diameter than the outside diameter of the coil, is placed in a socket within the lumen at the distal end of the catheter and the catheter is then moved into a vessel in order to place the coil at a desired position. Once the position is reached, a pusher wire with a piston at the end thereof is pushed distally from the proximal end of the catheter to thereby push the ball out of the socket in order to thereby release the coil at the desired position. Such a system is disclosed in U.S. Pat. No. 5,350,397, entitled, "Axially Detachable Embolic Coil Assembly." One problem with this type of coil placement system which utilizes a pusher wire which extends through the entire length of the catheter and which is sufficiently stiff to push an attachment ball out of engagement with the socket at the distal end of the catheter is that the pusher wire inherently causes the catheter to be too stiff with the result that it is very difficult to guide the catheter through the vasculature of the body.

Another method for placing an embolic coil is that of utilizing a heat releasable adhesive bond for retaining the coil at the distal end of the catheter. One such system uses laser energy which is transmitted through a fiber optic cable in order to apply heat to the adhesive bond in order to release the coil from the end of the catheter. Such a method is disclosed in U.S. Pat. No. 5,108,407, entitled, "Method And Apparatus For Placement Of An Embolic Coil." Such a system also suffers from the problem of having a separate element which extends throughout the length of the catheter with the resulting stiffness of the catheter.

Still another method for placing an embolic coil is disclosed in co-pending U.S. patent application Ser. No. 09/177,848, entitled "Embolic Coil Hydraulic Deployment System," filed on Oct. 21, 1998 and assigned to the same assignee as the present patent application. This patent application discloses the use of fluid pressure which is applied to the distal tip of the catheter for expanding the lumen in order to release the embolic coil.

Various embolic coil designs have been proposed for use with coil deployment systems such as the stretch resistant vaso-occlusive coil disclosed in U.S. Pat. No. 5,853,418, entitled "Stretch Resistant Vaso-occlusive Coils," which discloses a helically wound coil having a polymeric stretch resisting member extending through the lumen of the coil and fixedly attached to both the distal end and the proximal end of the coil. While the stretch resisting member prevents the coil from being stretched during use, this member which extends throughout the length of the coil tends to significantly reduce the flexibility of the coil. This reduced flexibility may present problems because in order to place vaso-occlusive coils into a desired location it is very important that the coil be very flexible.

SUMMARY OF THE INVENTION

The present invention is directed toward a vascular occlusive coil which may be placed at a preselected site within the vasculature and which exhibits the property of being stretch resistant while at the same time being very flexible. The coil may also be modified to vary the stiffness of the coil while at the same time retaining the stretch resistant characteristics of the coil. These and other features result in a vaso-occlusive coil which overcomes problems associated with prior embolic coils.

Accordingly, the present invention is directed toward a vaso-occlusive device for placement within the vasculature and includes an elongated helically wound coil having a proximal end, a distal end and a lumen extending therethrough. The coil is preferably formed of a plurality of turns of wire having a diameter of between about 0.0002 and 0.008 inches and the coil has an overall diameter of between about 0.006 and 0.055 inches. Substantially all of the turns from the proximal end of the coil to the distal end of the coil are spot welded to adjacent turns such that the spot welded joints between adjacent turns form a straight line which extends in a direction parallel to the longitudinal axis of the lumen of the coil. Also, the terms may be connected by other methods, such as by glueing or attachment by wrapping with thread.

In accordance with another aspect of the present invention, substantially all of the turns from the proximal end of the coil to the distal end of the coil are spot welded to adjacent coils in at least two locations such that the two spot welded joints between adjacent turns form two straight lines which extend in a direction parallel to the longitudinal axis of the lumen of the coil. In accordance with still another aspect of the present invention, the coil is formed of an alloy of which at least a portion is comprised of platinum, and preferably an alloy comprised of 92 percent platinum and 8 percent tungsten.

In accordance with still another aspect of the present invention, substantially all of the turns from the proximal end of the coil to the distal end of the coil are spot welded to an adjacent turn such that the spot welded joints between adjacent turns form a helical path which extends around the longitudinal axis of the coil.

In accordance with still another aspect of the present invention, substantially all of the turns of the coil from the proximal end to the distal end are spot welded to an adjacent turn at a first location such that the spot welded joints between adjacent turns form a straight line which extends in a direction parallel to the longitudinal axis of the lumen, and additionally selected ones of the turns are spot welded to an adjacent turn such that the additional welded joints form a straight line parallel to the first line of welded joints.

With the coil design of the present invention, the coil is prevented from stretching or unwinding while at the same time the coil retains a high degree of flexibility. In addition, with this design, it is possible to modify the degree of flexibility by bonding together different combinations of adjacent turns of the coil.

DESCRIPTION OF A PREFERRED EMBODIMENT

Figure 1:
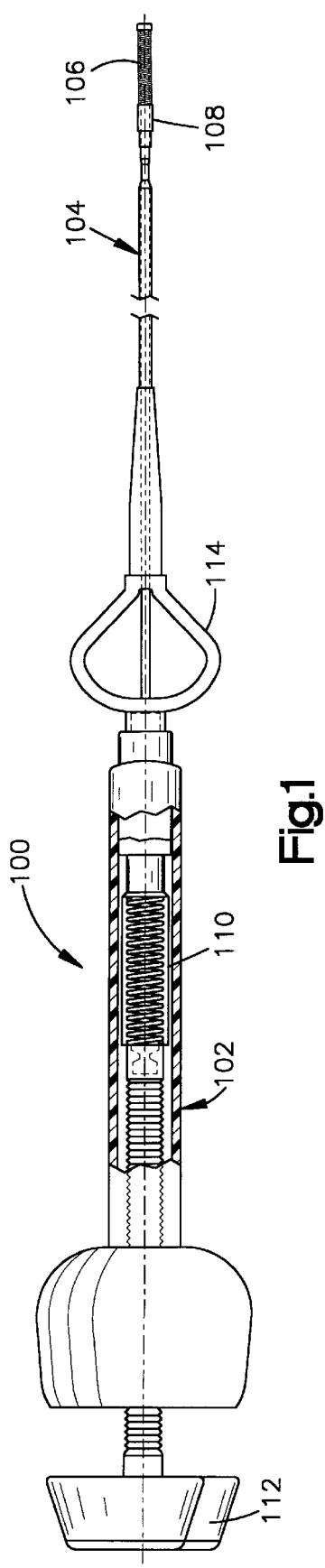
FIG. 1 is an enlarged, partially sectioned view of the hydraulic vascular occlusive coil deployment system.

FIG. 1 generally illustrates the vascular occlusive coil deployment system 100 which is comprised of a hydraulic injector or syringe 102, coupled to the proximal end of a catheter 104. An embolic coil 106 is disposed within the lumen of the distal end 108 of the catheter. The proximal end of the coil 106 is tightly held within the lumen of the distal section 108 of the catheter 104 until the deployment system is activated for release of the coil. As may be seen, the syringe 102 includes a threaded piston 110 which is controlled by a handle 112 for infusing fluid into the interior of the catheter 104. Also as illustrated, the catheter 104 includes a winged hub 114 for connection of the catheter 104 to a syringe or other hydraulic injector.

Figure 2:
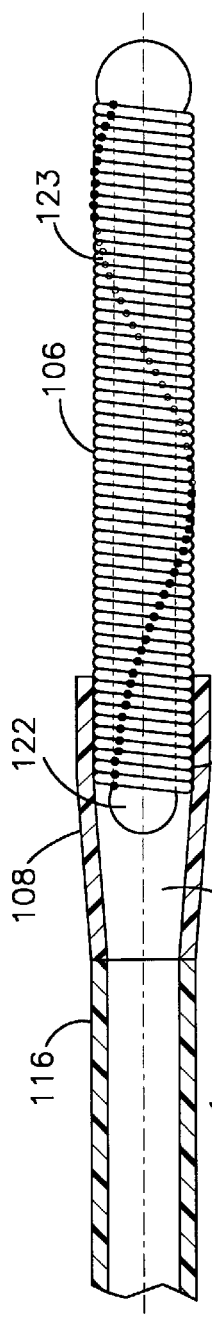
FIG. 2 is an enlarged partially sectioned view showing the distal end of the coil deployment system prior to deployment of the coil including an embolic coil of the present invention in which all of the turns are spot welded together along a helical path which extends around the central axis of the coil.

FIG. 2 illustrates in more detail the distal end of the catheter 104. The catheter 104 includes a proximal section 116 and the distal section 108. The proximal section 118 of the embolic coil 106 is disposed within the distal section 108 of the catheter and is tightly held within the lumen 120 of this distal section 108 prior to release of the coil. As may be appreciated, FIG. 2 illustrates the vascular occlusive coil deployment system prior to activation of the piston of the syringe and prior to release of the coil.

The embolic coil 106 may take various forms and configurations and may even take the form of a randomly wound coil, however, with the helical wound coil as illustrated in FIG. 2, the coil is provided with a weld bead or seal plug 122 which is disposed in a lumen 123 which lumen extends throughout the length of the coil 106. The seal plug 122 serves to prevent the flow of fluid through the lumen of the coil 106 so that when the coil 106 is placed in fluid-tight engagement with the lumen 120 the coil serves to provide a fluid-tight seal at the distal end of the catheter 104. Adjacent turns of the coil 106 at the proximal end 118 of the coil are preferably continuously welded together so that the welded turns of the coil in conjunction with the seal plug 122 provide a generally unitary structure which serves to plug or seal the distal end of the catheter in a fluid tight relationship.

Preferably, the proximal section 116 and the distal section 108 of the catheter 104 are formed of materials having different durometers. The proximal section 116 is preferably formed of Pebax material having a durometer in a range of about 62D to 75D. The proximal section is sufficiently flexible to transverse the vasculature of the human body, but is sufficiently rigid such that when a fluid pressure of approximately 90 to 450 psi is applied to the interior of this section of the catheter there is very little, if any, radial expansion of the walls of this section. On the other hand, the distal section 108 of the catheter is preferably formed of polymer material with a relatively low durometer which, exhibits the characteristic that when a fluid pressure of approximately 90 to 450 psi is applied to the interior of the catheter the walls of the distal section 108 expand radially, somewhat similar to the action of a balloon inflating, to thereby release the proximal end 118 of the coil 106. As may be appreciated, there are numerous materials which could be used to fabricate the proximal section 116 and distal section 108 of the catheter 104, however, the distal section 108 is preferably formed from a block copolymer such as Pebax having a durometer of between 25D and 55D with a durometer of 40D being the preferred durometer.

Figure 3:
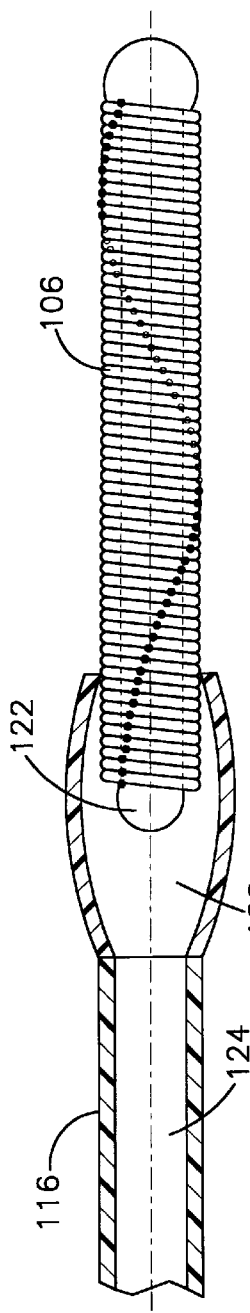
FIGS. 3 and 4 illustrate the sequential steps in the radial expansion of the distal tip of the coil deployment system as the embolic coil is released.
Figure 4:
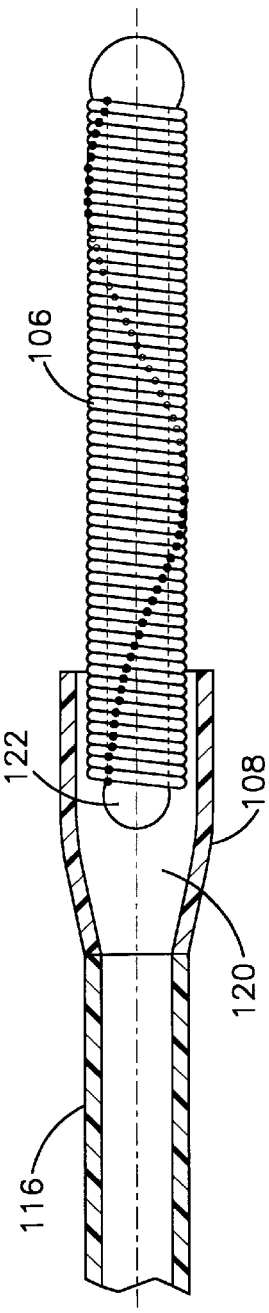

FIGS. 3 and 4 generally illustrate the coil release mechanism in action for the vascular occlusive catheter deployment system. More particularly, as shown in FIG. 3, when a hydraulic pressure is applied to the interior 120 of the catheter 104 the relatively low durometer distal section 108 of the catheter begins to expand radially, much as a balloon expands during the process of inflation. As the distal section 108 continues to expand radially there comes a point as illustrated in FIG. 4 in which the coil 106 becomes disengaged from the lumen of the distal section 108 and the coil is then released from the catheter and is deployed at that location within the vessel.

Figure 5:
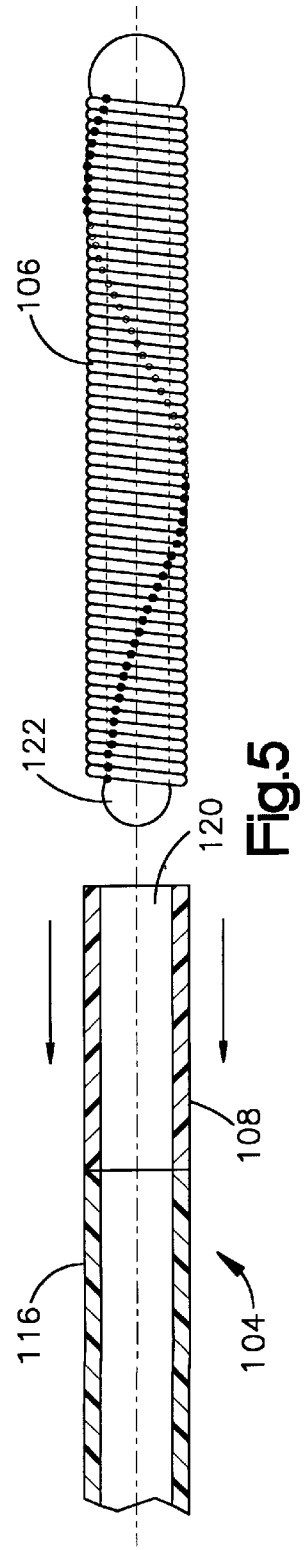
FIG. 5 illustrates the distal tip of the coil deployment system after release of the embolic coil; and, FIG. 6 is a plan view showing one embolic coil of the present invention in which all of the turns of the coil are spot welded together along two parallel lines.

As illustrated in FIG. 5, when the coil 106 has been released from the catheter 104 the catheter may then be withdrawn leaving the coil positioned at the desired site.

Figure 6:
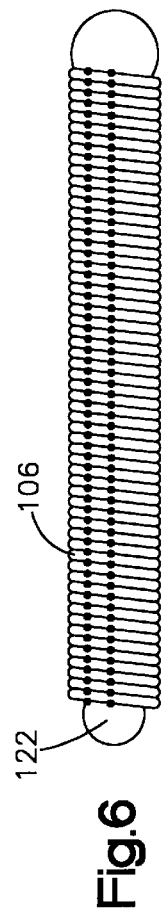
Figure 7:
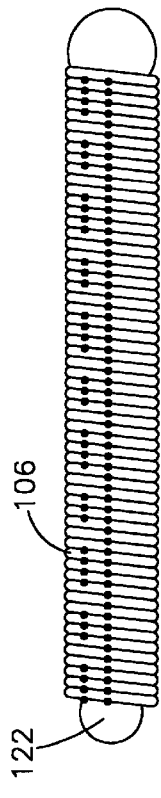
FIG. 7 is a plan view showing one embolic coil of the present invention in which all of the turns of the coil are spot welded together along a single line and certain of the turns are spot welded together along a second line parallel to the first line.

FIGS. 5, 6 and 7 illustrate three embodiments of the vasoocclusive coil of the present invention, however, it should be appreciated that there are numerous other possible embodiments of the present invention including other variations of the pattern of spot welding of turns of the coil. In these embodiments, the vaso-occlusion or embolic coil 106 is formed by winding a platinum alloy wire into a tightly wound helical configuration. The diameter of the wire is generally in the range of about 0.0002 to 0.008 inches. The outside diameter of the coil 106 is preferably in a range of about 0.006 to 0.055 inches. While the particular embolic coil 106 illustrated in FIGS. 5 through 8 is shown as being a straight coil it should be appreciated that embolic coils take the form of various configurations and may take the form of a helix, a random shape configuration or even a coil within a coil configuration.

With the embodiments of the coil illustrated in FIGS. 5 through 7 substantially all of the turns of the coil from the distal end to the proximal end of the coil are spot welded to an adjacent turn in order to prevent the coil from stretching or unwinding during placement. Alternatively, the adjacent turns may be bonded together by glueing or by use of a wrapping thread. Often times it is necessary to move a coil to a certain position within the vasculature and then to withdraw the coil back to a more proximal position. During the movement of the coil through the vasculature, particularly when the coil is being withdrawn to a more proximal position, it is possible to stretch or unwind the turns of the coil. If adjacent turns of the coil are spot welded to each other throughout the length of the coil the turns are prevented from separating at the juncture of the spot welds to thereby essentially prevent the coil from being stretched over its entire length.

FIG. 5 also illustrates an embodiment of the present invention in which adjacent turns of the coil are spot welded at a single location however the weld beads generally form a path which extends helically around the central axis of the lumen of the embolic coil.

FIG. 6 illustrates an embodiment of the present invention which includes two parallel rows of spot welds which extend along the length of the coil. Preferably, the spot bonding between adjacent coils is performed by laser welding of adjacent turns, alternatively the adjacent turns may be welded together using resistance welding. Accordingly, with this embodiment, the resulting structure includes two rows of weld points which extend along the length of the coil and generally in a direction parallel to the longitudinal axis of the coil.

FIG. 7 illustrates another embodiment of the present invention in which a single row of weld beads extend in a pattern along the length of the coil and in this case selected groups of three or four adjacent turns are also bonded together. The row of weld beads which extends from the distal end to the proximal end of the coil generally form a straight line parallel to the longitudinal axis of the coil and also the weld beads for the selected turns form a generally straight line parallel to the continuous line of weld beads.

A liquid silicon material (not shown) may be injected to fill the lumen of the proximal portion of the coil. The silicone material is then allowed to cure in order to further seal the proximal end of the coil to prevent fluid leakage through the turns of the coil. Also, as may be appreciated, instead of spot welding adjacent turns of the coil, the adjacent turns may be bonded by various other means such as, for example, by glueing or being attached by wrapping with thread.

As may be appreciated, each of the embodiments illustrates in FIGS. 6 through 7 provide for an embolic coil which is stretch resistant but a coil in which the flexibility is retained. Also, by adding various additional spot welds between selected coils it is possible to vary the overall stiffness of the embolic coil.

With the vaso-occlusive coil of the present invention it is possible to create a stretch resistant embolic coil having a high degree of flexibility, or alternatively a coil which may be modified by the appropriate combination of welding of adjacent turns in order to control the overall stiffness of the coil.

As is apparent, there are numerous modifications of the preferred embodiment described above which will be readily apparent to one skilled in the art, such as many variations and modifications of the coil including numerous coil winding configurations, or alternatively other types of implant devices, such as a vascular filter. Also, there are obviously variations of the syringe arrangement for applying a fluid pressure to the interior of the catheter, including many other fluid pressure generating systems for increasing the pressure within the interior of a catheter in order to cause the distal section of the catheter to expand. These modifications would be apparent to those having ordinary skill in the art to which this invention relates and are intended to be within the scope of the claims which follow.

That which is claimed is:

1. A vaso-occlusive device comprising:
   an elongated helically wound coil having a proximal end, a distal end and a lumen extending therethrough, said coil being formed of a plurality of turns of wire having a diameter of between about 0.0002 and 0.008 inches and said coil having a diameter of between about 0.006 and 0.055 inches; and
   substantially all of such turns from the proximal end of the coil to the distal end of the coil being welded to adjacent turns to form welded joints such that the welded joints between adjacent turns form a straight line which extends in a direction parallel to a longitudinal axis of the lumen of the coil.

2. A vaso-occlusive device as defined in claim 1, wherein substantially all of such turns from the proximal end of the coil to the distal end of the coil are spot welded to adjacent turns in at least two locations to form two spot welded joints such that the two spot welded joints between adjacent turns form two straight lines which extend in a direction parallel to a longitudinal axis of the lumen of the coil.

3. A vaso-occlusive device as defined in claim 1, wherein the coil is formed of an alloy of which at least a portion is comprised of platinum.

4. A vaso-occlusive device as defined in claim 2, wherein the coil is formed of an alloy of which at least a portion is comprised of platinum.

5. A vaso-occlusive device comprising:

an elongated helically wound coil having a proximal end, a distal end and a lumen extending therethrough, said coil being formed of a plurality of turns of wire having a diameter of between about 0.0002 and 0.008 inches and said coil having a diameter of between about 0.006 and 0.055 inches; and, substantially all of such turns from the proximal end of the coil to the distal end of the coil being spot welded to adjacent turns to form spot welded joints such that the spot welded joints between adjacent turns form a helical path which extends around a longitudinal axis of the coil.

6. A vaso-occlusive device as defined in claim 5, wherein the coil is formed of an alloy of which at least a portion is comprised of platinum.

7. A vaso-occlusive device comprising:

an elongated helically wound coil having a proximal end, a distal end and a lumen extending therethrough, said coil being formed of a plurality of turns of wire having a diameter of between about 0.0002 and 0.008 inches and said coil having a diameter of between about 0.006 and 0.055 inches;

and substantially all of such turns from the proximal end of the coil to the distal end of the coil being spot welded to adjacent turns at a first location to form spot welded joints such that the spot welded joints between adjacent turns form a first straight line which extends in a direction parallel to a longitudinal axis of the lumen, and selected ones of such turns additionally spot welded to adjacent turns at additional spot welded joints such that the additional spot welded joints form a second straight line parallel to the first straight line of spot welded joints.

8. A vaso-occlusive device comprising:

an elongated helically wound coil having a proximal end, a distal end and a lumen extending therethrough, said coil being formed of a plurality of turns of wire having a diameter of between about 0.0002 and 0.008 inches and said coil having a diameter of between about 0.006 and 0.055 inches; and substantially all of such turns from the proximal end of the coil to the distal end of the coil being bonded to adjacent turns to form bonded joints such that the bonded joints between adjacent turns form a straight line which extends in a direction parallel to a longitudinal axis of the lumen of the coil.

9. A vaso-occlusive device as defined in claim 8, wherein substantially all of such turns from the proximal end of the coil to the distal end of the coil are spot welded to an adjacent coil in at least two locations such that the two spot welded joints between adjacent turns form two straight lines which extend in a direction parallel to a longitudinal axis of the lumen of the coil.

* * * * *